United States Patent

Wentworth et al.

[11] Patent Number: 5,589,187
[45] Date of Patent: Dec. 31, 1996

[54] PROTECTIVE ENCAPSULATION OF MICRONUTRIENTS FOR INGESTION BY AVIAN SPECIES

[75] Inventors: Alice L. Wentworth; Bernard C. Wentworth, both of Madison, Wis.

[73] Assignee: Wisconsin Alumni Research Foundation, Madison, Wis.

[21] Appl. No.: 482,736

[22] Filed: Jun. 7, 1995

[51] Int. Cl.⁶ ........................................ A61K 9/48
[52] U.S. Cl. .................. 424/439; 424/442; 424/451; 424/491; 424/497; 424/492; 514/951; 426/72; 426/805; 426/807
[58] Field of Search ..................... 424/451, 490, 424/491, 492, 497, 477, 482, 439, 442, 499

[56] References Cited

U.S. PATENT DOCUMENTS

| | | | |
|---|---|---|---|
| 3,265,629 | 8/1966 | Jensen | 252/316 |
| 3,619,200 | 11/1971 | Ferguson et al. | 99/2 |
| 4,230,687 | 10/1980 | Sair et al. | 424/22 |
| 4,389,419 | 6/1983 | Lim et al. | 426/72 |
| 4,803,085 | 2/1989 | Findley | 426/69 |
| 4,822,620 | 4/1989 | Chamberlain et al. | 426/2 |
| 4,983,403 | 1/1991 | Ardaillon et al. | 426/2 |
| 4,996,067 | 2/1991 | Kobayashi et al. | 426/96 |
| 5,098,718 | 3/1992 | Ardaillon et al. | 426/2 |

*Primary Examiner*—James M. Spear
*Attorney, Agent, or Firm*—DeWitt Ross & Stevens SC

[57] ABSTRACT

The invention relates to a method of encapsulating digestible micronutrients or other additives within coatings which are indigestible by other than mechanical means, and the encapsulated additives. The invention includes a method for coating digestible micronutrients with indigestible polymers which can be mechanically broken down within the gizzards of avian species where the digestible micronutrients may be absorbed. The encapsulated additives are stabilized against degradation under harsh conditions within silos, and can be added directly to ensiled vegetable matter without chemical degradation of the encapsulated additive.

24 Claims, No Drawings

PROTECTIVE ENCAPSULATION OF MICRONUTRIENTS FOR INGESTION BY AVIAN SPECIES

FIELD OF THE INVENTION

The present invention relates generally to a method of encapsulating digestible micronutrients, vitamins, trace elements, medicinals, and other additives within coatings which are indigestible by other than mechanical means. The invention also relates to the encapsulated additives. More specifically, the present invention relates to a method for coating digestible micronutrients with indigestible polymers which can be mechanically broken down within the gizzards of avian species where the digestible micronutrients may be absorbed.

DESCRIPTION OF THE PRIOR ART

As the agricultural sector of the economy grows more competitive, cost-effective methods of feeding farm animals are becoming increasingly desirable. As a result, farmers are exploring the use of less expensive and more readily available forms of animal feed for farm animals which are normally fed commercial feed. One possibility that is currently being explored is the use of field corn, peas and alfalfa-based silage as feed for poultry such as turkeys and chickens. The use of such silage is attractive because it is far less expensive than commonly used commercial poultry feed. Silage prices in 1994 were approximately 50% of that of commercial poultry feed.

Initially, research by the present inventors, Wentworth et al. (unpublished), discovered that silage feed containing ensiled soybeans results in increased embryonic death when fed to turkeys, presumably due to the production of toxic amines during the decomposition of the ensiled materials. The increased embryonic death rates returned to normal when soybeans were excluded from the silage. It was also found that the caloric content of silage feed did not significantly affect fecundity. Most significantly, it has been found that the acidic, high-temperature and moisture conditions during ensilation tend to break down many of the beneficial nutrients in the ensiled materials, most particularly vitamin E and some of the B vitamins (particularly thiamin and biotin). Since insufficient intake of these nutrients, particularly vitamin E, thiamin and biotin drastically decreases fecundity, Wentworth et al. concluded that raw silage was not an appropriate feed for poultry. Cattle and other mammals, on the other hand, are able to ingest silage for extended periods of time with no ill effects because their digestive tracts contain microbes which allow the synthesis of missing nutrients. Avian species, which lack these microbes, will suffer from low egg production, low fertility and low hatchability if fed solely silage.

Wentworth et al. also performed experiments wherein the above-noted nutrients and fat were added to silage after its removal from the silo (disensilation) and prior to being fed to poultry. When the nutrients were intermixed with the silage using an auger-type mixer, and then fed to poultry, fecundity returned to normal levels.

However, despite Wentworth et al.'s finding that post-ensilation addition of supplemental nutrients to silage renders it nutritionally suitable for use as poultry feed, use of such a supplemented silage is still not cost-effective for two reasons:

First, farmers would be required to purchase, meter, and mix nutrients into silage after it is disensiled. The extra time and equipment required for mixture of nutrients after disensilation increases the expense of the silage feed to the point where it is competitively priced compared to commercial feeds. The expense cannot be decreased by adding nutrients in bulk to the silage before it is disensiled, e.g., by blowing powdered nutrients into the silo, because the environment of the silo would rapidly degrade the nutrients.

Second, the pH of the silage after its removal from the silo tends to degrade these nutrients even when they are added to the silage after disensilation. Therefore, silage with added supplemental nutrients tends to lose nutritional value unless the supplemental nutrients are added only a very short time before feeding.

Additionally, many of the nutrients themselves have a relatively short shelf life. Therefore, the cost of the silage feed is also increased because farmers would regularly be required to purchase supplemental nutrients in small quantities, and to restock supplies when the nutrients lose their potency.

One possible solution to these problems is presented by prior art coatings for animal and human feed supplements. An overview of these coatings follows:

U.S. Pat. No. 3,265,629, to Jensen, discloses a protective coating for nutrient granules to be incorporated into animal feed. The coating protects the nutrients from decomposition by air and moisture, but slowly breaks down over an extended period of time when exposed to enzymes or the environmental conditions in farm fields. This gives the encapsulated nutrients longer shelf life, while still enabling them to be easily digested by farm animals. Encapsulated nutrients are produced by coating the individual nutrient particles with a solid lipid material, suspending the coated particles in an aqueous solution of encapsulating material, and inducing phase separation to cause the encapsulating material to solidify about the nutrient particles. The encapsulated particles then precipitate from the aqueous solution.

U.S. Pat. No. 4,803,085, to Findley, discloses a digestible film coating suitable for use on solid feed-supplement blocks. Nutrients such as vitamins and minerals may be incorporated within the coating.

U.S. Pat. No. 4,389,419, to Lim et al., discloses a process for encapsulating oils and oil-soluble materials (such as vitamins A, D, and E) by surrounding the oil with an alginate gel coating which is readily digested by mammals. During storage, the alginate gel coating protects the oil within from oxidative degradation.

U.S. Pat. No. 4,996,067, to Kobayashi et al., discloses a composition and method for coating teed additives such as basic amino acids and proteins to avoid their decomposition in the rumen. The coating allows the feed additives to be efficiently digested and absorbed in the abomasum or a subsequent digestive organ.

U.S. Pat. No. 5,098,718, and U.S. Pat. No. 4.983,403, both to Ardaillon et al., also disclose coating compositions which can be used to coat feed additives for ruminants. The coatings protect the encapsulated nutrients when they enter the rumen, but are subsequently degraded when exposed to the enzymes of the small intestine.

U.S. Pat. No. 4,230,687, to Sair et al., discloses digestible coatings for vitamins, flavors, and other substances intended for ingestion by either human or non-human animals.

It must be noted, however, that the prior art coating processes are not suitable for protecting nutrients within a silo. In general, any coating which can be enzymatically digested by an animal will also be readily destroyed by the high temperatures, microbes and acidity found within a silo. Therefore, nutrients coated using the prior art coatings will lose their effectiveness as the environmental conditions within the silo degrade the coating, and then the nutrients encapsulated therein. Therefore, these prior art processes do not provide a solution to the problem of nutrient degradation after nutrients are added to ensiled matter.

The prior art also discloses other possible methods of preserving the nutrient content of ensiled materials. U.S. Pat. No. 4,822,620, to Chamberlain et al., note that the nutrients within ensiled materials are lost both by decomposition, as discussed above, and by the slow leaching of water-soluble nutrients through the silage and out of the silo. Chamberlain et al. solve the latter type of nutrient loss by dispersing water-absorbent, water-swellable particles of synthetic polymer within the silage. The nutrient-bearing liquid silage effluent is absorbed by the polymer and retained within the silage, thereby allowing the soluble nutrients to be consumed by silage-eating animals. This method, however, does not offer any solution to the problem of nutrient degradation due to high-temperature and pH of the ensiled feedstuffs.

SUMMARY OF THE INVENTION

The encapsulation process of the present invention provides poultry farmers with a feed having a nutritional value equal to that of commercial poultry feed, and the cost-effectiveness of silage feeds.

The present invention includes a method of encapsulating foodstuff additives which comprises coating a foodstuff additive with a first proteinaceous coating to form protein-coated grit particles, and then encapsulating the protein-coated grit particles within an enzymatically indigestible plastic to form plastic-encapsulated grit particles having a plastic coating capable of being mechanically degraded.

The present invention also includes a method of encapsulating avian-specific foodstuff additives which comprises dissolving casein in an aqueous solution of gelatin to yield a protein-rich solution, adding an avian foodstuff additive to the protein-rich solution to yield an additive-protein mixture, drying the additive-protein mixture to yield protein-coated grit particles, and dispersing the protein-coated grit particles within an enzymatically plasticized indigestible plastic matrix to form plastic-encapsulated grit particles having a plastic coating capable of being mechanically degraded within gizzards of avian species.

The present invention is additionally drawn to an avian feed comprising silage, and a plurality of plastic-coated grit particles, the plastic-coated grit particles including at least one foodstuff additive encapsulated within a first inner protein coating, and a second outer plastic coating.

The present invention allows coated nutrients (hydrophilic and hydrophobic vitamins, amino acids, trace elements, and the like), pharmaceuticals (antibiotics, anti-parasitic agents, hormones, and the like), and other foodstuff additives to be rapidly and economically prepared for addition to ensiled matter, finished silage, or commercial animal feed. The coated additives take the form of a nutrient grit which may be blown or otherwise added to a silo in bulk. This allows for cost-effective addition of nutrients to silage by eliminating the need to store, meter, and mix nutrients within the silage after it is removed from the silo.

Further, the protective coating protects the additives in the grit from the hot, acidic, and oxidative environment of a silo.

The present invention allows nutrients to retain their full nutritional value for extended periods of ensilation, where the prior art coatings fail. After disensilation, the grit-laden silage may be fed to poultry, or other avians, whose gizzards are able to mechanically break down the protective coating of the nutrient grit. The broken coating, which is largely indigestible by enzymatic means, passes harmlessly through the digestive tracts of the birds while the exposed foodstuff additives are absorbed. The coated additives thereby enhance the nutritional content of silage to the level required for productive poultry.

Additionally, the coated nutrients of the present invention may be more economically added to silage even after it has been removed from the silo. Prior to the present invention, it has not been cost-effective to add some nutrients to silage for three reasons: First, the pH of the silage destroys much of the effectiveness of the nutrients, even if they are coated by the prior art methods. As a result, prior art nutrients are generally added to silage in excess quantities because it is expected that only a portion of the nutrients will remain undegraded before ingestion by poultry. Second, the short shelf life of the nutrients makes them inefficient to use because they must regularly be purchased and restocked in small lots. Third, mixing the nutrients and the disensilated silage requires extra time and equipment.

The present invention obviates the first two problems because the coated nutrients are protected from the acidity of the silage, and are also protected from going stale upon long-term storage (which is mainly caused by oxidative or photolytic degradation). Additional savings are achieved because excess nutrients do not have to be included. Additionally, since the cost of presently described supplemented silage feed is approximately half that of commercial feed, the cost of any metering or mixing equipment needed to inject the nutrient grit into a silo will generally pay for itself quite rapidly.

Furthermore, feed additives other than nutrients can be coated and used as a feed supplement. As an example, pharmaceuticals such as antibiotics, anti-parasitic agents, hormones, prophylactic medicinals, and the like may be coated by use of the present invention. A specific example would be encapsulation of anti-protozoa agents to prevent coccidiosis.

Advantageously, use of the present invention prevents all non-avian farm animal species from digesting the pharmaceutical. Such species lack a gizzard and thus lack the mechanical digestion means for breaking down the coating. Since the coating is indigestible to mammals, the encapsulated material will merely pass through the digestive tracts of mammalian species without effect.

Alternative embodiments of the present invention include encapsulation of birth control compounds for inclusion in feed as part of a pest control scheme, e.g., for pigeons in metropolitan areas.

The present invention may be also used to encapsulate feed supplements for use in commercial and pre-packaged avian feed. The coated supplements will be protected from oxidation and degradation, thereby extending the shelf life of the feed. In addition, the coating protects the supplements sufficiently that the use of butylated hydroxytoluene (BHT), butylated hydroxyanisole (BHA), and similar preservatives to protect the supplements can be eliminated.

As noted above, certain feed supplements for poultry are inappropriate for use in mammalian species. As a result, the Food and Drug Administration currently requires that different feed supplements be distinctively colored so that the supplements are not accidentally misadministered. Since feed supplements which are encapsulated by the coating of the present invention can only be digested by avian species, the need for these colorants is eliminated.

In light of the above discussion, it is an aim of the present invention to provide an encapsulated, silage-based, avian feed stock that maintains its effective nutrient content during ensilation, the encapsulation of which is mechanically degradable within avian gizzards, and which is nutritionally sufficient to maintain the health and fecundity of avian species.

Another aim of the present invention is to provide a method of encapsulating feed supplements which protects the supplements from chemical, thermal, and photolytic degradation.

These and other aims and objects of the present invention will become clear upon a complete reading of the "Detailed Description" and attached claims.

DETAILED DESCRIPTION OF THE INVENTION

Silage is regularly used to feed ruminant livestock. "Silage" as used herein is defined to mean vegetable matter, often fodder, which has been converted into a feed for livestock through various processes of anaerobic acid fermentation within a silo. A wide variety of vegetable matter, such as corn, beans, peas, alfalfa, and the like, can be converted within silos into silage. As used herein, the term "silo" encompasses any and all types of structures used to produce silage. Included among these structures are vertical silos, trench silos, silage bags, "harvestores," and the like. Such structures are well known to those in the art.

As described above, in an effort to lower feed costs, attempts have been made to feed silage to avians, most notably poultry for human consumption or egg production. Included in the latter class of avians are birds regularly raised in commercial agriculture, including chickens of all types (bantam weights, game hens, egg-producers, broilers, etc.), turkeys, ducks, geese, pheasant and ratites (e.g., ostrich, emu, rhea). Other regularly encountered avians include grouse, woodcock, pigeons, and other avian species either desired as foodstuffs or sporting birds, or reviled as pests. This is an illustrative list, and is not to be construed as limiting in any fashion.

Silage, however, is not nutritionally complete for many avian species, including the commercially-produced poultry species listed above. Many amino acids and vitamins (most notably, B vitamins) found within raw vegetable matter are degraded during the ensilation process. Ruminant animals can survive and breed when fed only silage owing to rumen microorganisms which synthesize the needed nutrients de novo. Avian species, however, are unable to biosynthesize the nutrients destroyed during ensilation and therefore suffer decreased egg production, fertility and hatchability when fed unsupplemented silage.

Silage is especially low in B vitamins, particularly thiamin. This is due to the formation of at least ten different thiaminases which are formed during ensilation. During ensilation, these thiaminases catalyze the breakdown of thiamin. As a result, the finished silage is effectively depleted of thiamin, as well as other B vitamins. Therefore, in order to serve as a more nutritionally complete food source for avians, commercially-produced poultry species in particular, silage must be supplemented with B vitamins and other nutrient additives.

As noted above, silage can be produced from a wide variety of vegetable matter capable of being ensiled within a silo, where it is enzymatically degraded. Typical vegetable matter included in silage may include high moisture content corn, alfalfa, field peas, soy beans, and the like. A preferred silage composition for the present invention is presented in Table 1 (based upon dry weight basis):

TABLE 1

| |
| --- |
| 43.0% high-moisture corn |
| 17.8% alfalfa |
| 17.8% peas |
| (10.0% soybean)* |
| 5.0% added fat |
| 3.5% $CaCO_3$ |
| 1.9% $DiCal-PO_4$ |
| 0.5% salt |
| 0.5% synthetic grit |

*soybean added after removal from silo

The vegetable matter is preferably chopped to an average length of approximately one-eighth inch length prior to ensilation. In the preferred embodiment, soybeans are excluded from ensilation because it is believed that they result in the formation of toxic amines which reduce embryonic viability in avians. Cooked soybeans can optionally be added to the silage after ensilation to increase the protein content of the silage.

The present invention includes a foodstuff additive encapsulation method which allows the additives, which are often chemically and thermally degradable, to be added directly to vegetable matter to be ensiled. By adding the encapsulated additives described herein directly to a silo, the present invention obviates the need for post-ensilation supplementation of the resultant silage. The silage is nutritionally complete upon disensilation. The encapsulation of the additives protects them from chemical and thermal degradation during silage production.

Table 2 summarizes an ongoing study comparing the fecundity of turkey hens fed silage into which the presently claimed synthetic grit containing B vitamins is added to the fecundity of turkey hens fed silage into which B vitamins are mixed directly. As is clearly shown in the table, the fecundity of the turkeys fed the presently described plastic-coated grit compares quite favorably with both the control group and the group led vitamin B-supplemented silage. As noted above, however, the plastic-coated vitamin B particles resists degradation within the silage, thereby imparting long-lasting nutritional goodness to the silage.

The data contained in Table 2 is reported for a 20 week period. The hens are inseminated every 14 days. The silage used in the study is as close as possible in composition to the preferred silage composition described above. The silage was prepared within an airtight silo. Emphasis was placed on keeping the silage isocaloric and isonitrogenous with the control. The fertility and hatchability are based only on odd day (day of the year) production.

TABLE 2

Three Year Summary of Fecundity Data of Turkey Hens Fed Synthetic Grit Containing B Vitamins as Compared to Mixing B Vitamins with Silage after Ensiling or Commercial Type Control Ration

| Year and Treatment | Percent Production | Percent Fertile | Percent Hatch |
|---|---|---|---|
| 1993 Control | 70.0 | 91.5 | 75.5 |
| Silage + Vitamins[a] | 68.3 | 91.6 | 71.5 |
| Silage + Grit Containing Vitamins[b] | 71.2 | 92.6 | 71.6 |
| 1994 Control | 55.1 | 91.4 | 78.4 |
| Silage + Vitamins[a] | 59.0 | 91.7 | 83.1 |
| Silage + Grit Containing Vitamins[b] | 53.4 | 92.6 | 82.0 |
| 1995[c] Control | | | 78.4 |
| Silage + Vitamins[a] | | | 83.1 |
| Silage + Grit Containing Vitamins[b] | | | 82.0 |

[a]The B vitamins were mixed with the silage after is was removed from the silo.
[b]The B vitamins were in synthetic grit fed as part of the silage.
[c]There are 30 more days of data collection for 1995 and only part of the information has been summarized.

Any type of foodstuff additive can be encapsulated using the presently described method. Typical additives include, but are not limited to water and oil-soluble vitamins, amino acids, hormones, medicinal agents such as antibiotics, anti-fungals, anti-parasitic agents, anti-coccidiosis agents, anti-virals, prophylactic medicinals, and the like; and essential minerals and micronutrients. Of particular importance is the encapsulation of vitamin E and some of the B vitamins, especially thiamin. This is because silage is notably low in these vitamins. The encapsulation protects the foodstuff additive from being chemically or enzymatically degraded until such time as the outer coating is mechanically compromised.

Granulation of the Foodstuff Additive

A preliminary step of the process generally entails pulverizing and/or granulating the foodstuff additive if it is not already particulate in nature. The additives may be granulated by any known conventional granulating method, such as extrusion granulation, fluidized granulation, rolling granulation, or agitation granulation. (See, for instance, Kobayashi et al., U.S. Pat. No. 4,996,067, incorporated herein by reference for its teaching of conventional granulation methods.) Conventional binders, fillers, and excipients, so long as physiologically acceptable, may be added to facilitate granulation. The method of granulation is not critical to the present invention.

Protein-Coating the Foodstuff Additive

The foodstuff additive is then coated with at least one proteinaceous coating. Additional proteinaceous coatings may be applied to further insulate the additive particles. The protein coating protects the additive from being directly contacted with the outer plastic coating.

Any type of suitably cohesive and adhesive protein coating may be employed. The main criteria here are that the protein coating be sufficiently adhesive so as to bind to the foodstuff additive particles, and sufficiently cohesive so as to completely surround and encapsulate the additive particles.

The preferred protein coat is formed using an aqueous casein and gelatin solution. The foodstuff additive is introduced into the protein-rich solution, mixed thoroughly, and dried to yield protein-coated grit particles.

More preferably still, an amount of casein equal to the amount of foodstuff additive to be encapsulated is introduced into a sufficient quantity of a 10% gelatin solution to dissolve the casein. The casein/gelatin solution may be gently heated to speed dissolution of the casein. The foodstuff additive is then slowly introduced into the casein/gelatin solution with constant stirring. The solution is then poured into molds, or spread into thin layers, and allowed to dry completely.

It must be noted that any type of known coating method can be employed to apply the protein coating to the additive particles. Such methods include spray coating, fluidized coating methods, and centrifugal fluidized coating methods. Such methods are well known to those in the art, as shown by Kobayashi et al., U.S. Pat. No. 4,996,067, incorporated herein by reference for its teaching of conventional coating methods.

After thorough drying, the protein-coated grit particles may then be comminuted to a desired size using any conventional means, such as passing the grit through a screen. Optionally, the protein-coated grit may be coated with a second coating of protein. The second protein coating may be applied in the same manner as the first. The grit is again dried and comminuted to a desired mesh size. An exemplary mesh size for protein-coated grit for consumption by turkeys would be approximately 2 mm.

Comminution of the grit may be accomplished by any means known in the art. For example, the grit may be pulverized using roller mills, ball mills, pug mills, screens, sieves, and the like.

Applying a Plastic-Coating to the Protein-Coated Grit

The protein-coated grit particles formed above are then coated with an enzymatically indigestible plastic layer.

The plastic used to coat the grit must be enzymatically indigestible by ruminants, other mammals, and even avians. The plastic coating should also be non-toxic to commonly encountered farm and domestic animals. While not mandatory, it is preferred that if ingested by non-avian species, the plastic coating should shield the grit such that the plastic-coated grit particles pass through the digestive tract of the animal intact.

At the same time, the plastic coating should be sufficiently weak so as to be mechanically degradable within the gizzards of birds which ingest the plastic-coated grit. Once the plastic coating is structurally breached, the food additive within is exposed and subsequently digested by the birds. The breached plastic coating is then harmlessly excreted.

The plastic coating must also be high-temperature stable, and impervious to those enzymes produced during ensilation. As used here, "high-temperature stable" means stable at those temperatures normally encountered during ensilation. A wide variety of different enzymes are produced during ensilation, along with the production of a large amount of heat. The plastic coating must protect the food additive from contact with the enzymes, and from direct exposure to the heat of the ensilation process. In this manner, the encapsulated foodstuff additive is protected from degradation during ensilation within a silo.

Any type of plastic which fits the above physical description can be used in the present invention. The plastic can be thermosetting or thermoplastic, synthetic or natural, a homopolymer, a copolymer, or a mixture of polymer resins.

The preferred plastic is a mixed plastic resin containing polyester resin, styrene monomer, and methylmethacrylate. Such resins are sold under the trademarks CAROPLASTIC (Carolina Biological Supply Co., Burlington, N.C., USA), and CASTOLITE-AP and POLYLITE® (Reichhold Chemicals, Inc., Durham, N.C., USA).

When unpolymerized, the above resins are clear liquids. Upon addition of a catalyst, such as methyl ethyl ketone peroxide (MEKP), the resins cure to a hard, impermeable, and unreactive finish. The cured plastic is enzymatically indigestible, and non-toxic.

In the same manner as noted above for the application of the protein coating, the plastic coating may be applied to the protein-coated grit particles in any known and suitable fashion.

Preferably, the protein-coated grit particles are mixed with a sufficient amount of plastic to completely coat the grit, and a suitable amount of catalyst is added to cure the plastic. The plastic/grit mixture is then poured into molds, or spread in thin layers, and the plastic allowed to cure. In the preferred embodiment, about 1000 ml of CAROPLASTIC and 6.2 ml of MEKP catalyst are used for each 500 grams of protein-coated grit.

The ratio of protein-coated grit to plastic resin will vary depending upon the desired mechanical stability of the finished product, the mesh size of the grit, and the species of animal which will be fed the final product. For instance, if a more mechanically stable plastic coating is desired, the ratio of protein-coated grit to plastic is decreased, thereby forming a thicker plastic coating around the grit particles. This approach can also be used to increase the final dimensions of the grit, which may be desired when feeding the grit to relatively large birds such as turkeys. Increasing the ratio of protein-coated grit to plastic yields a grit having a lower overall plastic content, and having a thin plastic coating which is more easily degraded. This may used to deliver a larger effective dose of the foodstuff additive to the birds.

When the plastic resin has cured completely, the protein-coated grit particles are completely surrounded by an enzymatically-impervious plastic coating. The plastic and protein-coated grit aggregate is comminuted as described above to yield plastic-coated grit of any desirable mesh. The plastic-coated grit is indigestible by enzymatic means, and will pass through the digestive tracts of mammals, including ruminants, unchanged.

The final size of the grit can be altered depending upon the type of avian to which the grit is to be fed. In turkeys, for instance, a suitable final particle diameter would be about 10 mm in diameter. The grit can be formulated to yield particles of a smaller size for feeding smaller birds. Any type of bird (e.g.. bantam chickens, broiler chickens, egg producing species and types, quail, grouse, pheasant, ostrich, turkeys, etc.) will benefit nutritionally from feeding with the plastic-coated grit particles.

When the plastic-coated particles are ingested by avian species as grit for the birds' gizzards, the mechanical action within the gizzard will breach the plastic coating, thereby exposing the protein-coated grit within. The protein coat, as well as the encapsulated foodstuff additive is then enzymatically digested in the birds' gut.

The outermost plastic coating may also be varied in thickness to protect the core nutrient material under differing ensilation conditions. Here, the structural rigidity of the plastic shell may be increased or decreased depending upon the length of time taken for complete ensilation, or the size of the silo. If, for instance, the materials to be ensiled are known to require an especially long ensilation period, the plastic coating may be made thicker to ensure that the grit particles will remain intact during the extended ensilation period. The thicker plastic coating requires a longer period to be broken down by the gizzard.

Similarly, in very large vertical silos, grit particles in the lower portions of the silo will experience a large amount of pressure from the material within the upper portions of the silo. Here, it may be desirous to have grit particles with a substantial plastic coating to guarantee the structural integrity of the particles. The opposite may be true of bag and trench silos, where the ensiled materials are not stacked to such large heights. Here, a relatively smaller plastic coating would likely suffice to protect the encapsulated additive.

The plastic coated grit may be added to vegetable matter prior to ensilation, or the grit may be added to silage upon disensilation. The grit may also be added to commercial feed to alter its nutritional content. Preferably the grit is added to vegetable matter prior to its being ensiled. In this fashion, the resultant silage may be made nutritionally complete for avians, and can be fed to birds immediately upon disensilation. This obviates the need to add nutrients to the silage subsequent to its being removed from a silo, which saves both time and the expense of metering and mixing equipment.

EXAMPLE

The following example is for illustrative purposes only. It is understood that the example does not limit the invention claimed herein in any manner.

Protecting B Vitamins in Silage Feed for Turkeys

This example illustrates the formulation of a synthetic grit containing encapsulated B vitamins for incorporation into silage-based turkey feed.

First, appropriate quantities of the various B vitamins (thiamin, riboflavin, pyridoxine, cyanocobalamin, etc.) are measured and thoroughly mixed. For this example, the "appropriate" quantity of B vitamins was based upon the livestock nutritional requirements promulgated by the National Research Council.

The mixed B vitamins are then added to a protein rich paste containing an equal weight of casein dissolved in a 10% aqueous solution of gelatin. The resulting protein paste, which now contains added B vitamins, is spread in a thin layer (2 mm thickness) and air dried.

Once dried, the vitamin and protein (casein and gelatin) mixture is passed through a 2-mm screen. Optionally, the 2-mm particles may be again placed in a 10% aqueous gelatin solution, dried, and screened. This results in a protein-coated vitamin B grit. The protein coat protects the vitamins from the organic phase of the plastic encapsulation to be applied.

The protein-coated grit is then mixed with a plastic coating agent. Here, 1000 ml of clear embedding plastic (CAROPLASTIC), and 6.2 ml catalyst (methyl ethyl ketone peroxide) was added for each 500 g of protein-coated grit. The plastic mixture is then spread in a thin layer, or placed into molds, and allowed to cure. This yields a plastic-coated grit.

For turkeys, a relatively large bird, the plastic grit is passed through a 10 mm screen.

The 10 mm grit is then mixed with silage prior to ensilation. At disensilation, the silage is then nutritionally suitable for turkey feed without further supplementation.

An identical, or substantially similar procedure, is used to encapsulate any number of different feed supplements. The process parameters will vary depending upon the nature of the supplement being encapsulated. Such variations are within the skill of those in the feed formulation art. The varios ratios of supplement to protein coating, and protein-coated grit to plastic matrix can also be varied accordingly.

The ultimate size of the plastic-coated grit can be modified depending on the size and species of bird being fed.

It is understood that the present invention is not limited to the above-described embodiments, but encompasses all embodiments thereof within the scope of the attached claims.

What is claimed is:

1. A method of encapsulating foodstuff additives comprising:
    (a) coating a foodstuff additive with a first proteinaceous coating to form protein-coated grit particles; and
    (b) encapsulating the protein-coated grit particles within an enzymatically indigestible plastic to form plastic-encapsulated grit particles having a plastic coating capable of being mechanically degraded within gizzards of avian species, and wherein the enzymatically indigestible plastic is selected from the group consisting of thermoplastic or thermosetting polyesters, polystyrenes, polyacrylates, co-polymers thereof, and combinations thereof.

2. An avian feed comprising silage and a plurality of plastic-coated grit particles, said plastic-coated grit particles including at least one foodstuff additive encapsulated within a first inner protein coating, and a second outer plastic coating, wherein said at least one foodstuff additive is selected from the group consisting of at least one vitamin, at least one medicinal agent, at least one anti-protozoan agent, at least one anti-coccidiosis agent, at least one anti-parasitic agent, and combinations thereof.

3. The avian feed of claim 2, wherein said second outer plastic coating comprises a mixture of polyethylene resin, styrene, and methylmethacrylate.

4. The avian feed of claim 2, wherein said second outer plastic coating is selected from the group consisting of thermoplastic or thermosetting polyesters, polystyrenes, polyacrylates, co-polymers thereof, and combinations thereof.

5. The avian feed of claim 2, wherein said first inner protein coating comprises casein and gelatin.

6. A method of encapsulating foodstuff additives comprising:
    (a) coating a foodstuff additive with a first proteinaceous coating to form protein-coated grit particles;
    (b) comminuting the protein-coated grit particles so as to pass through a 2-mm mesh; and then
    (c) encapsulating the protein-coated grit particles within an enzymatically indigestible plastic to form plastic-encapsulated grit particles having a plastic coating capable of being mechanically degraded.

7. The method of claim 6, further comprising the steps of subsequent to comminuting the protein-coated grit particles, coating the protein-coated grit particles with a second proteinaceous coating, and comminuting the protein-coated grit particles a second time so as to pass through a 2-mm mesh.

8. The method of claim 7, wherein in said coating steps, the food additive and the protein-coated grit are coated with a proteinaceous coating comprising casein and gelatin.

9. The method of claim 7, wherein in said encapsulating step, the protein-coated grit particles are encapsulated with a plastic capable of being mechanically degraded within gizzards of avian species.

10. The method of claim 7, wherein in said encapsulating step, the protein-coated grit particles are encapsulated with a plastic resin comprising polyester resin, styrene, and methylmethacrylate.

11. The method of claim 7, wherein in said encapsulating step, the protein-coated grit particles are encapsulated with a plastic resin selected from the group consisting of thermoplastic or thermosetting polyesters, polystyrenes, polyacrylates, co-polymers thereof, and combinations thereof.

12. A method of encapsulating foodstuff additives comprising:
    (a) coating a foodstuff additive with a first proteinaceous coating to form protein-coated grit particles wherein said foodstuff additive is selected from the group consisting of at least one vitamin, at least one amino acid, at least one medicinal agent, at least one anti-protozoan agent, at least one anti-coccidiosis agent, at least one anti-parasitic agent, and combinations thereof; and
    (b) encapsulating the protein-coated grit particles within an enzymatically indigestible plastic to form plastic-encapsulated grit particles having a plastic coating capable of being mechanically degraded.

13. The method of claim 12, wherein in said coating step, a foodstuff additive selected from the group consisting of B vitamins, vitamin E, and combinations thereof, is coated.

14. A method of encapsulating avian foodstuff additives comprising:
    (a) dissolving a water-soluble protein in an aqueous solution of gelatin to yield a protein-rich solution;
    (b) adding an avian foodstuff additive to the protein-rich solution to yield an additive-protein mixture;
    (c) drying the additive-protein mixture to yield protein-coated grit particles;
    (d) dispersing the protein-coated grit particles within an enzymatically indigestible plastic matrix to form plastic-encapsulated grit particles having a plastic coating capable of being mechanically degraded within gizzards of avians.

15. The method of claim 14, wherein in said dissolving step, casein is dissolved in a 10% aqueous solution of gelatin.

16. The method of claim 14, wherein in said adding step, an avian foodstuff additive selected from the group consisting of at least one vitamin, at least one amino acid, at least one medicinal agent, at least one anti-protozoan agent, at least one anti-coccidiosis agent, at least one anti-parasitic agent, and combinations thereof, is added to the protein-rich solution.

17. The method of claim 16, wherein in said adding step, an avian foodstuff additive selected from the group consisting of B vitamins, vitamin E, and combinations thereof, is added to the protein-rich solution.

18. The method of claim 14, wherein in said dispersing step, the protein-coated grit particles are dispersed within a plastic matrix comprising polyethylene resin, styrene, and methylmethacrylate.

19. The method of claim 14, wherein in said dispersing step, the protein-coated grit particles are dispersed within an enzymatically indigestible plastic matrix selected from the group consisting of thermoplastic or thermosetting polyesters, polystyrenes, polyacrylates, co-polymers thereof, and combinations thereof.

20. A silage-based avian feed comprising:

silage, and at least one encapsulated foodstuff additive made by
(a) coating a foodstuff additive with a first proteinaceous coating to form protein-coated grit particles; and
(b) encapsulating the protein-coated grit particles within an enzymatically indigestible plastic to form plastic-encapsulated grit particles having a plastic coating capable of being mechanically degraded.

21. The silage-based avian feed of claim 20, wherein said silage is devoid of soybeans, and said at least one encapsulated foodstuff additive includes one or more B vitamins.

22. A silage-based avian feed comprising:
silage, and at least one encapsulated foodstuff additive made according to the method of claim 13.

23. The silage-based avian feed of claim 22, wherein said silage is devoid of soybeans, and said at least one encapsulated foodstuff additive includes one or more B vitamins.

24. The silage-based avian feed of claim 23, wherein said at least one encapsulated foodstuff additive includes thiamine.

* * * * *

UNITED STATES PATENT AND TRADEMARK OFFICE
CERTIFICATE OF CORRECTION

PATENT NO. : 5,589,187
DATED : December 31, 1996
INVENTOR(S) : Wentworth, et. al.

It is certified that error appears in the above-identified patent and that said Letters Patent is hereby corrected as shown below:

Column 1, Line 8 add -- The invention was made with United States Government support awarded by USDA #58-1265-8-002 Hatch Funds. The United States Government has certain rights in this invention. -- as the first paragraph.

Column 2, Line 51, delete "teed" and substitute -- feed -- therefor.

Column 8, Line 54, delete "maimer" and substitute -- manner -- therefor.

Column 9, Line 29, insert the word "be" between the words "may" and "used".

Signed and Sealed this

Seventh Day of April, 1998

Attest:

BRUCE LEHMAN

*Attesting Officer*          *Commissioner of Patents and Trademarks*